(12) United States Patent
Wilks

(10) Patent No.: US 12,203,849 B2
(45) Date of Patent: Jan. 21, 2025

(54) ANALYSIS OF MIXED VOLATILE COMPOUNDS

(71) Applicant: Dylan Elmer Wilks, New London, NH (US)

(72) Inventor: Dylan Elmer Wilks, New London, NH (US)

(73) Assignee: ORANGE PHOTONICS, INC., Elkins, NH (US)

( * ) Notice: Subject to any disclaimer, the term of this patent is extended or adjusted under 35 U.S.C. 154(b) by 239 days.

(21) Appl. No.: 17/716,985

(22) Filed: Apr. 8, 2022

(65) Prior Publication Data

US 2022/0326153 A1 Oct. 13, 2022

Related U.S. Application Data

(60) Provisional application No. 63/173,543, filed on Apr. 12, 2021.

(51) Int. Cl.
*G01N 21/552* (2014.01)
*B01L 3/00* (2006.01)
*B01L 7/00* (2006.01)
*G01N 25/14* (2006.01)
*G01N 33/00* (2006.01)

(52) U.S. Cl.
CPC ...... *G01N 21/552* (2013.01); *B01L 3/502715* (2013.01); *B01L 7/52* (2013.01); *G01N 25/14* (2013.01); *B01L 2300/0654* (2013.01); *B01L 2300/1805* (2013.01); *B01L 2300/1894* (2013.01); *G01N 33/0047* (2013.01); *G01N 2201/023* (2013.01)

(58) Field of Classification Search
CPC .. G01N 21/552; G01N 25/14; G01N 33/0047; G01N 2201/023; B01L 3/502715; B01L 7/52; B01L 2300/0654; B01L 2300/1805; B01L 2300/1894
See application file for complete search history.

(56) References Cited

U.S. PATENT DOCUMENTS

| | | | | |
|---|---|---|---|---|
| 3,528,278 | A * | 9/1970 | Sterling | G01N 21/552 385/12 |
| 5,460,973 | A * | 10/1995 | Schrader | G01N 21/552 422/82.11 |
| 7,581,877 | B1 * | 9/2009 | Zarrabian | G01N 25/68 374/18 |
| 2004/0108472 | A1 * | 6/2004 | Maruo | G01N 21/552 250/504 R |
| 2004/0154414 | A1 * | 8/2004 | LaCourse | G01N 30/14 73/863.23 |

(Continued)

*Primary Examiner* — Edmond C Lau
*Assistant Examiner* — Noah J. Haney
(74) *Attorney, Agent, or Firm* — Morgan, Lewis & Bockius LLP

(57) ABSTRACT

Analytic sensors and methods utilize an attenuated total reflection (ATR) crystal to detect volatile compounds in an arrangement that reduces interference from compounds other than the one of interest. In particular, the components in the measurement stream are limited to those having volatilities close to that of the analyte of interest, which may be identified based on, for example, the temperature of the ATR crystal and the "dwell time"—i.e., an interval of substantially constant temperature as the ATR crystal is heated.

15 Claims, 2 Drawing Sheets

(56) References Cited

U.S. PATENT DOCUMENTS

| | | | |
|---|---|---|---|
| 2004/0189982 A1* | 9/2004 | Galarneau | G01N 21/552 |
| | | | 356/135 |
| 2013/0114082 A1* | 5/2013 | Sailor | G01N 21/171 |
| | | | 356/402 |
| 2016/0369214 A1* | 12/2016 | Mosher | C12C 11/003 |
| 2017/0131204 A1* | 5/2017 | Sieben | G01N 21/0332 |
| 2020/0182894 A1* | 6/2020 | Nieuwenhuis | G01N 35/00584 |

* cited by examiner

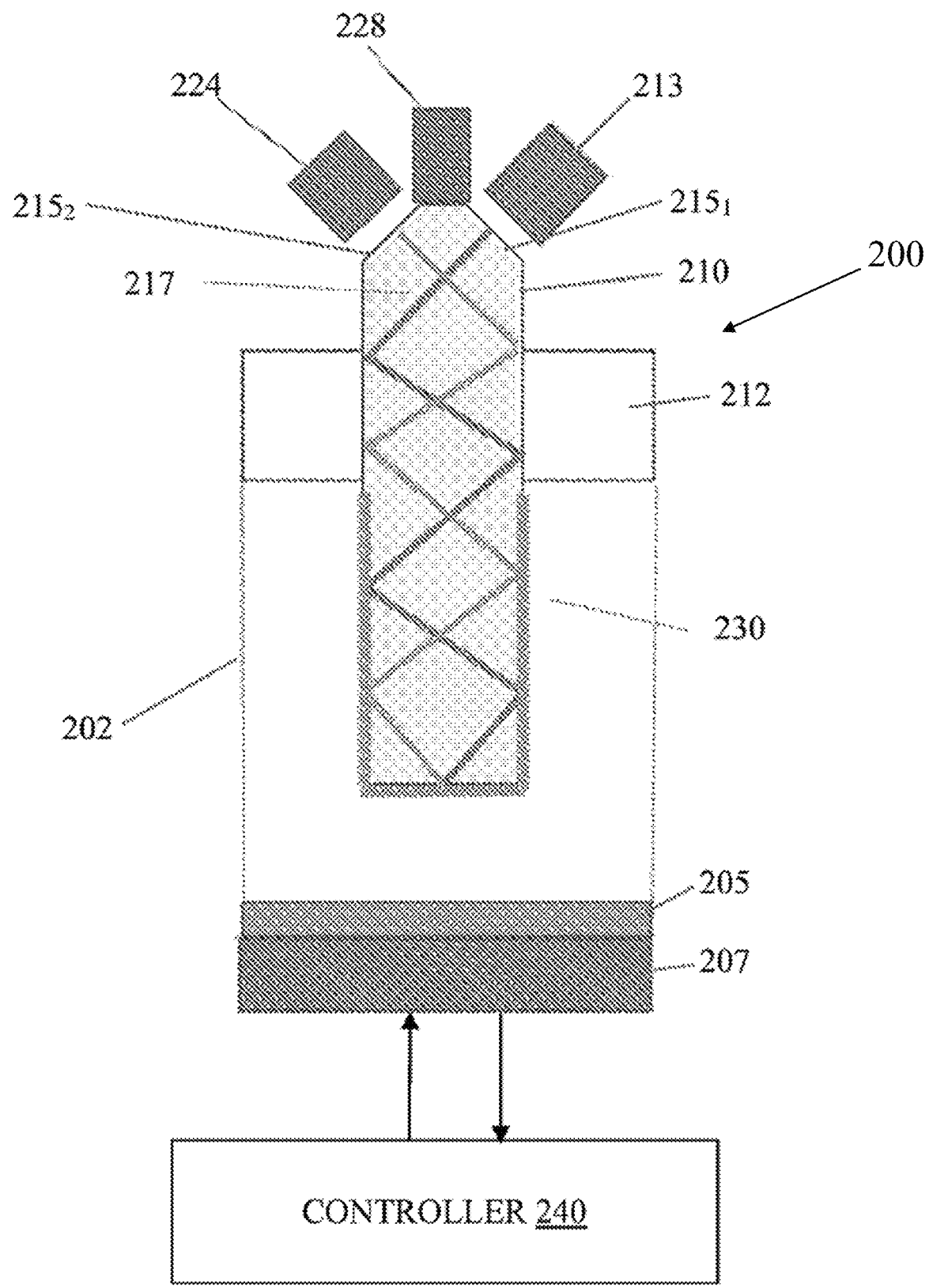

ANALYSIS OF MIXED VOLATILE COMPOUNDS

CROSS-REFERENCE TO RELATED APPLICATION

This application claims priority to, and the benefit of, U.S. Provisional Patent Application No. 63/173,543, filed on Apr. 12, 2021, which is hereby incorporated by reference in its entirety.

FIELD OF THE INVENTION

The present invention relates to the preparation and analysis of volatile compounds in liquid, solid and vaporous samples.

BACKGROUND

Volatile compounds are common chemicals that tend to evaporate quickly even at room temperature. These chemicals can vary widely in chemical structure, as well as toxicity and usefulness. Current technology for detecting and analyzing volatile compounds falls into two broad categories: portable, non-specific measurement typically utilizing flame or photo-ionization techniques, and laboratory-based measurements such as headspace gas chromatography coupled with mass spectrometry; the latter can identify and quantify many species of volatile compounds. Thus, simple systems tend to be non-specific, while the ability to discriminate among multiple analytes in a volatile mixture typically involves specialized, complex, and expensive equipment.

Accordingly, there is a need for conveniently deployed analytic sensing systems that exhibit improved discrimination capability.

SUMMARY

Embodiments of the invention utilize a known type of analytic sensor—namely, an attenuated total reflection (ATR) crystal—to detect volatile compounds in an arrangement that reduces interference from compounds other than the one of interest. As is well known, when light travels from a medium of high refractive index (e.g., an ATR crystal) to a medium of low refractive index (a volatile sample), some of the light is reflected back into the high-refractive-index medium. At a particular angle of incidence, almost all of the light is reflected back, a condition called total internal reflection (TIR). The reflection is not total, however, in that some of the light energy escapes the crystal invisibly and extends a small distance (0.1-5 μm) beyond the surface; this phenomenon is called the evanescent wave. As a result, some amount of the light penetrating beyond the crystal is absorbed by sample condensed or adsorbed on the crystal surface. If the radiation is infrared (IR), this absorbance may be translated into the IR spectrum of the sample. Suitable ATR crystals include diamond, ZnSe, Ge, Si, and KRS-5 (a 40:60 mixture of thallium bromide and iodide).

Typical ATR-based measurement systems are nonspecific, i.e., they do not discriminate among compounds in a volatile mixture. In embodiments of the present invention, however, this is done by first limiting the components in the measurement stream to those having volatilities close to that of the analyte of interest. As a result, all components other than those that condense on the crystal concurrently with an analyte of interest are will be excluded. This exclusion step reduces the complexity of the measurement and increases the accuracy by reducing the number of interfering compounds present.

Next, the individual compounds in the condensed mixture are resolved based on their volatilities, which, again, are close enough so they all condense on the crystal under particular conditions (e.g., at a particular temperature). A more volatile chemical will have a higher boiling point. As an example, α-pinene has a boiling point of 157° C. and β-caryophyllene which has a boiling point of 245° C. When a sample with both of these components is heated, α-pinene appears first on the crystal and then later β-caryophyllene. Conversely, myrcene has a boiling point of 167° C., and would condense on the crystal at a similar time to α-pinene, so these will need to be separated. It is found that distinct substances with boiling points differing by approximately 25-50° C.

As the sample begins to collect on the crystal face, detector readings are collected. In various embodiments, the temperature of the sample and the crystal are adjusted over time. The temporal pattern of temperature increase as energy is delivered to the system (e.g., via a heating plate) reflects the latent heats of the various compounds in the mixture, which are progressively driven off the crystal. From this pattern, and based on a calibration if appropriate, the identities of the compounds in the mixture may be deduced.

For example, a very volatile analyte may need very little sample heat and a very cold crystal, but later in the same testing procedure the heat may be increased on the sample side, forcing a less volatile component into a vapor phase, and then subsequently condensing on the crystal. If necessary, the crystal may be heated in between to drive off the original sample. Since the volatilities of the different compounds may vary, the detector readings may occur for an extended period, and data collected at different time periods may be used to determine concentration of different compounds.

Accordingly, in one aspect, the invention pertains to an apparatus for detecting an analyte in a mixed sample containing the analyte and other analytes. In various embodiments, the apparatus comprises an attenuated ATR crystal having an outer surface for adsorbing the sample thereon; a light source for directing light into the ATR crystal; means for detecting light from the light source that has passed through the ATR crystal; a heat source for heating the sample bed; and a controller for monitoring a temperature as the sample bed is heated and, based at least in part on the monitored temperature, identifying the analyte. The apparatus may include a cooling device for cooling the ATR crystal to cause condensation of the sample on the outer surface thereof and/or a heating device for heating the crystal to drive off sample after the analyte is identified. The heating and cooling functions may, in some embodiments, be performed by the same device.

The controller may be configured to derive a dwell time from the monitored temperature, where the dwell time corresponds to an interval of substantially constant temperature as the ATR crystal is heated. The controller may be configured to identify the end of the dwell time based on a sharp increase in temperature and/or by monitoring the slope of the increase in the temperature. In various embodiments, the controller is configured to identify the analyte based also on the dwell time.

In another aspect, the invention relates to a method of detecting an analyte in a mixed sample containing the analyte and other analytes. In various embodiments, the method comprises the steps of heating the sample; adsorbing the sample onto an ATR crystal; directing light into the ATR crystal; detecting light from the light source that has passed through the ATR crystal; and monitoring the temperature as the sample is heated and, based at least in part on the monitored temperature, identifying the analyte.

In various embodiments, the method further comprises cooling the ATR crystal to cause condensation of the sample on the outer surface thereof. The identifying step may comprise deriving a dwell time from the monitored temperature, where the dwell time corresponds to an interval of substantially constant temperature as the sample is heated. The end of the dwell time may be identified based on a sharp increase in temperature and/or by monitoring the slope of the increase in the temperature. The analyte may identified based also on the dwell time.

The heat may be provided by a heat source or by the ambient environment. In some embodiments, the method includes heating the ATR crystal to drive off sample following identification of the analyte.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The term "consists essentially of" means excluding other materials that contribute to function, unless otherwise defined herein. Nonetheless, such other materials may be present, collectively or individually, in trace amounts. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which:

FIG. 2 schematically illustrates a representative detector implementing embodiments of the invention in a vertical configuration.

DETAILED DESCRIPTION

Figure 1:
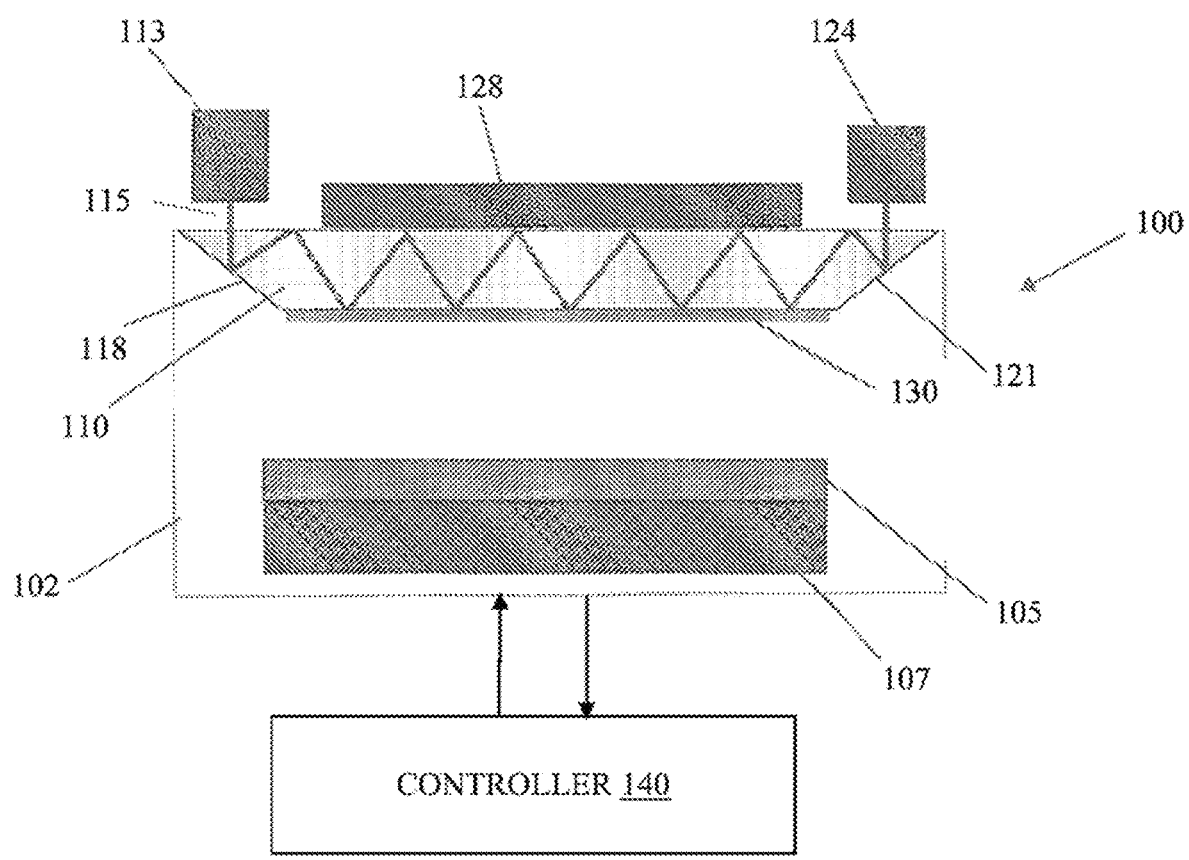
FIG. 1 schematically illustrates a representative detector implementing embodiments of the invention in a horizontal configuration.

Representative embodiments of an analyte detection and identification system in accordance herewith are illustrated in FIGS. 1 and 2. FIG. 1 shows a horizontally oriented system 100 that includes a housing 102 having therein a sample container 105 and a temperature-altering element 107 (e.g., a plate capable of heating, cooling or both) under the sample container 105. An ATR crystal 110 forms the ceiling of the housing 102. An IR light source 113 directs IR radiation along a light path 115 onto the flat top surface of the ATR crystal 110. The ATR crystal includes a bevel 118 so that IR radiation propagates by reflection along the length of the crystal, emerging through the top surface via reflection from an opposed bevel 121. At least a portion of the IR radiation emerging from the top surface of the ATR crystal 110 is received by a conventional IR detector 124. In one embodiment, the detector 124 is a pyroelectric infrared detector, e.g., the LME-336-63 device supplied by InfraTec GmbH. The detector 124 may use a single element (e.g., with a variable filter) multiple elements with corresponding fixed filters. Alternatives include Fabry-Perot detectors (e.g., the InfraTec LFP-80105C-337 device), which can detect different wavelengths of light. Another alternative is a Fourier Transform infrared (FT-IR) system, which may use mercury cadmium telluride (MCT) detectors.

To permit cycling of heating and cooling intervals, another temperature-altering element 128, which may be capable of heating, cooling, or both, can be disposed atop the ATR crystal 110. The ATR crystal 110 may be metallized on one or more surfaces to aid in the transfer of heat to the crystal and/or to increase reflectance or block attenuated TIR at some locations. Generally, a crystal with more reflections will be more sensitive than crystals with fewer reflections.

The IR source 113 may be a pulsed IR blackbody emitter, a constant blackbody emitter or a fixed-wavelength emitters. The emitter choice may be determined in part by the detector type. The IR detector 124 may be a fixed-wavelength detector, a detector array or a spectrometer-based detection system (e.g., a spectrometer with multiple photodetectors). These components are conventional, and the precise wavelengths to be used in a particular application are determined straighforwardly, and without undue experimentation, based on the analyte matrix.

In the horizontal orientation shown in FIG. 1, the crystal is shaped such that attenuated total internal reflection (TIR) occurs on the underside of the crystal surface where volatile samples will condense as indicated at 130. In the vertical orientation 200 shown in FIG. 2, TIR occurs on multiple (e.g., three) crystal surfaces. Once again the system 200 includes a housing 202, which may directly contain the sample 205 over a temperature-altering element 207 (e.g., a plate capable of heating, cooling or both) within or under the housing 202. The ATR crystal 210 is retained within a cap 212 removably joined to the housing 202 (e.g., by threads or compression fit) and forming its ceiling. A portion of the ATR crystal 210 extends into the interior of the housing 202. An IR light source 213 directs IR radiation through a beveled edge 2151 along the light path 217; the IR radiation propagates down and back up the height of the ATR crystal 210 by TIR, exiting from a second beveled edge 2152. If the ATR crystal 210 is circular in section, the edges 2151 and 2152 are part of a continuous sidewall, but in other configurations, the edges 2151 and 2152 are separate. At least a portion of the IR radiation emerging from the second beveled edge 2152 is received by an IR detector 224. Another temperature-altering element 228, which may be capable of heating, cooling, or both, can be disposed atop the ATR crystal 210. In operation, volatile samples will condense as indicated at 230 along the outer surface(s) of the ATR crystal 210.

The temperature-altering elements 107, 128, 207, 228 are individually and collectively optional depending on the characteristics of the volatile compounds to be measured. The ATR crystal 110, 210 may be cooled for measurement, while, additionally or alternatively, the sample bed may be heated in order to promote condensation on the ATR crystal. A compound that easily condenses at room temperature may not require cooling. A cooling element 128, 228 may be active, i.e., thermoelectric, fluid-cooled, etc., or passive, such as cooling fins or heat sinks. A temperature-altering element 128, 228 may include both cooling and heating elements, the latter to assist in driving off compounds after measurement has occurred.

The temperature-altering element 107, 207, if included, generally provides heating and may be any suitable form of heating element or plate. Its inclusion or operation depends on the characteristics of the volatile compounds to be measured. A compound that easily volatilizes at room temperature may not require heating. The temperature-altering element 107, 207 may have a receptacle for receiving a liquid or solid sample for heating. Otherwise, the sample may be held in a separate sample container or may fill a portion of the housing 202. The housing 102, 202 may be reversibly sealed in order to retain sample around the ATR crystal 118, 218 and may be valved in order to facilitate control of sample entry. If sampling directly from the environment, a housing is not necessary.

A controller 140, 240 may be configured to initiate sampling, control the IR source 113, 213 and detector 124, 224, heating and/or cooling, and interpret detector signals as described below. The controller 140, 240 may be implemented in hardware, software or a combination of the two. For embodiments in which the functions are provided as one or more software programs, the programs may be written in any of a number of high level languages such as PYTHON, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80×86 assembly language if it is configured to run on a PC. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In operation, the ATR 110, 210 is either exposed to the environment or, in the case of a closed system where samples are not measured directly from the environment, samples are collected. The controller 140, 240 then activates the IR emitter 113, 213 and collects the baseline signal from the IR detector 124, 224. This may involve cleaning the ATR crystal and collecting detector signals from the clean crystal, or alternatively a baseline sample matrix can either be placed on the ATR crystal directly or analyzed as a sample would be. Collecting a baseline sample matrix reduces interference associated with the signals resulting from desired compounds (which can cause performance degradation).

A representative analysis sequence is as follows. In the case of a closed system, a sample is placed on the heating plate 107, 207. If the sample is gaseous, it is introduced into a sample container via syringe, pump or similar mechanism. In the case of direct environmental analysis, the system is placed in an area where the analysis will take place. For quantitative analysis, the amount of sample may be delivered at a specific weight or volume. Alternatively, the collection of data may be used to generate qualitative results. For example, the dwell time (as described below) may be used to determine environmental levels of volatile components. In a closed system, the temperature-altering element 107, 207, if present, is operated by the controller 140, 240 to impart heat to the sample (in the case of a closed system) or to the ATR crystal 110, 210 (in the case of an open system), raising the temperature of the sample to a level that allows volatilization of components to be analyzed. The particular heating program used may vary depending on the volatile components to be measured.

The temperature-altering element 128, 228, if present, is operated by the controller 140, 240 to cool/heat the ATR crystal 110, 210 and thereby facilitate faster condensation of volatiles on the crystal faces. The particular cooling program used may vary depending on the volatile components to be measured. As the sample begins to collect on the crystal face, readings from the detector 124, 224 are collected by the controller 140, 240. Since the volatilities of the different compounds may vary, the detector readings may occur for an extended period, and data collected at different time periods may be used to determine concentration of different compounds. Once data collection is complete, the controller 140, 240 analyzes the collected data based on a calibration. In particular, for a particular analyte at a specific sample temperature, the temperature of the ATR crystal 110, 210 and the "dwell time"—that is, the amount of time the sample and/or crystal remains at a constant temperature as heat energy is added from the temperature-altering element 107, 207, corresponding to the latent heat of one of the sample components—will be characteristic of an analyte. Once a particular measurement is complete, the ATR crystal 110, 210 may be heated by the temperature-altering element 128, 228 to drive off the current sample being measured and prepare for the next sample.

The dwell time is easily identified if the signal shows a sharp temperature transition at the end of a relatively flat interval. For example, at the start of measurement, the heating plate 107, 207 will begin to add energy to the sample bed. Once the temperature of the bed reaches 157° C., α-pinene will begin boiling, and thus will begin accumulating on the face of the ATR crystal 110, 210. At this point, the ATR crystal will no longer rise in temperature due to the latent heat of the α-pinene. The period during which the temperature does not change is considered the dwell time for α-pinene. During this α-pinene dwell time, the detector will read the spectroscopic data from the ATR crystal 110, 210 where the α-pinene has condensed. Therefore, α-pinene can be identified and quantified by the combination of dwell time and spectroscopic data.

Once the temperature of the sample heating plate 107, 207 begins to rise again, the dwell time is complete. As the sample plate temperature continues to rise, the ATR crystal will reach a second dwell point corresponding to a second analyte. For example, when the temperature reaches 245° C., β-caryophyllene will begin to boil off and the ATR crystal 110, 210 will again no longer rise in temperature, defining the dwell time for β-caryophyllene. If no sharp temperature transition occurs, the slope of the increase in temperature over the dwell time can be analyzed. For example, if an analyte is present at low concentration, the signal may rise sharply as the analyte is driven off the ATR crystal 110, 210; whereas if the sample is very concentrated, the signal level may rise slowly due to the larger concentration of sample on the crystal face. For example, once the sample bed reaches close to 157° C., i.e., 152-162° C., the temperature of the ATR crystal 110, 210 is monitored for α-pinene as it condenses on the crystal face. If the temperature rises slowly during this period for a given energy input to the heating plate 107, 207, it corresponds to a higher concentration of α-pinene due to the larger total latent heat of the higher concentration sample. If the temperature rises quickly during this period, less analyte is present since less energy was required to drive off the sample from the crystal face. Hence, the combination of the dwell time and rise pattern of the signal at the end of the dwell time may indicate not only the analyte but its concentration.

It may be necessary in some cases to calibrate the system 100, 200 in order to deliver quantitative results. Calibration may be accomplished using any of several approaches, including analyzing known calibration standards or reference materials that contain specific amounts of target compounds; analyzing samples that have previously been analyzed using a laboratory or other referee method; or normalizing system signals to a previously calibrated system so that the system responds to compounds in a similar way to the master system. In the latter case, calibration may be necessary only on one master system and subsequent systems with similar performance are assigned calibration data from the master system.

Any calibration samples analyzed may be collected by either directly placing the samples on the crystal face or measuring the calibration sample in the same way that an unknown sample is collected. Once calibration data is collected, the data is converted (e.g., by the controller 140, 240 or by a stand-alone computer) into a calibration curve or model that describes system performance using conventional tools well-known to those skilled in the art. In particular, a specific analyte, a sample temperature, crystal temperature and dwell time are related by the calibration process. Depending on the detector 124, 224, multiple analytes may have overlapping analytical conditions and still be detected separately by the detector (for example, they may have very different infrared spectra but similar volatility). In one approach, the sample is initially at room temperature and the crystal is initially below room temperature. Heat is added to raise the temperature of the sample, and decreasingly volatile components are measured. Typically this is done at a few different temperatures or along a temperature ramp.

For example, sample mixtures of various concentrations may be first created—e.g., α-pinene and β-caryophyllene are both mixed in three standard concentrations together, i.e., calibration standard #1 contains 100 ppm α-pinene and 100 ppm β-caryophyllene; calibration standard #2 contains 200 ppm α-pinene and 200 ppm β-caryophyllene; and calibration standard #3 contains 300 ppm α-pinene and 300 ppm β-caryophyllene. The calibration may begin by taking a baseline reading of detector signals with both the ATR crystal 110, 210 and sample plate at room temperature. Next, calibration sample #1 is added to the sample bed and the sample bed begins heating. As the temperature of the bed approaches the boiling point of α-pinene at 157° C., data is collected on the system including the rise in temperature of the ATR crystal 110, 210, the spectroscopic information from the ATR crystal and detector and the temperature of the sample bed. As the sample bed continues to heat, it will eventually approach 245° C., which is the boiling point of β-caryophyllene. Again temperature and detector data is collected. Once the system has reached a set temperature and all data has been collected, the system is cooled and prepared for the next calibration sample. Calibration standard #2 and #3 are subjected to the same process, and the data from all three runs may be used to generate a characteristic response for both α-pinene and β-caryophyllene, allowing the system to calculate unknown quantities of both analytes in a mixture.

Systems and methods in accordance herewith offer numerous advantages. The combination of ATR with the ability to intentionally condense components onto the crystal allows them to be analyzed free from interference due to samples that are not similarly volatile. The ability to control cooling and heating allows for measurement of potentially many compounds in a single sample, since over the analysis time several components may condense at different times and at different rates. The disclosed approach can be used for solids, liquids and gases, and can accommodate many different compounds in complex matrices.

Systems described herein combine the sample matrix improvements of the laboratory-based headspace analysis but reduce the complexity significantly. Typically in headspace analysis, a sample is heated and then some of the gas at the top of a sample vial is removed and analyzed. The present approach directly analyzes the headspace by intentionally re-condensing the sample onto a surface that facilitates IR analysis.

Embodiments of the disclosed technology allow for measurement of individual components or chemical classes of components, which previously required laboratory analytical techniques, since in general, current portable and low cost volatile component analyzers are non-specific. Such embodiments may involve only modest user input and involvement, and the overall system cost may be lower than that of current analytic instruments capable of discriminating among compounds in a mixed sample.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. Apparatus for detecting an analyte in a mixed sample containing the analyte and other analytes, the apparatus comprising:
   an attenuated total reflection (ATR) crystal having an outer surface for adsorbing the mixed sample thereon;
   a light source for directing light into the ATR crystal;
   means for detecting light from the light source that has passed through the ATR crystal;
   a heat source for heating the mixed sample; and
   a controller for monitoring a temperature as the mixed sample is heated and, based at least in part on the monitored temperature, identifying the analyte;
   wherein the controller is configured to derive a dwell time from the monitored temperature, the dwell time corresponding to an interval of substantially constant temperature as the ATR crystal is heated.

2. The apparatus of claim 1, further comprising a cooling device for cooling the ATR crystal to cause condensation of the mixed sample on the outer surface thereof.

3. The apparatus of claim 1, further comprising a heating device for heating the ATR crystal to drive off the mixed sample after the analyte is identified.

4. The apparatus of claim 1, wherein the controller is configured to identify an end of the dwell time based on a sharp increase in temperature.

5. The apparatus of claim 1, wherein the controller is configured to monitor a slope of an increase in the temperature to identify an end of the dwell time.

6. The apparatus of claim 1, wherein the controller is configured to identify the analyte based also on the dwell time.

7. A method of detecting an analyte in a mixed sample containing the analyte and other analytes, the method comprising using the apparatus of claim 1 to perform the steps of:
- heating the mixed sample;
- adsorbing the mixed sample onto an attenuated total reflection (ATR) crystal;
- directing light into the ATR crystal;
- detecting light from the light source that has passed through the ATR crystal; and
- monitoring a temperature as the mixed sample is heated and, based at least in part on the monitored temperature, identifying the analyte.

8. The method of claim 7, further comprising the step of cooling the ATR crystal to cause condensation of the mixed sample on the outer surface thereof.

9. The method of claim 7, wherein identifying the analyte comprises deriving a dwell time from the monitored temperature, the dwell time corresponding to an interval of substantially constant temperature as the mixed sample is heated.

10. The method of claim 9, wherein an end of the dwell time is identified based on a sharp increase in temperature.

11. The method of claim 10, wherein a slope of an increase in the temperature is monitored to identify an end of the dwell time.

12. The method of claim 9, wherein the analyte is identified based also on the dwell time.

13. The method of claim 7, wherein the heat is provided by a heat source.

14. The method of claim 7, wherein the heat is provided by the ambient environment.

15. The method of claim 7, further comprising the step of heating the ATR crystal to drive off the mixed sample following identification of the analyte.

\* \* \* \* \*